United States Patent [19]

Mikulicz

[11] 4,324,936
[45] Apr. 13, 1982

[54] BUTANE ISOMERIZATION PROCESS

[75] Inventor: Michael Z. Mikulicz, Palatine, Ill.

[73] Assignee: UOP Inc., Des Plaines, Ill.

[21] Appl. No.: 220,498

[22] Filed: Dec. 29, 1980

[51] Int. Cl.³ .............................................. C07C 2/58
[52] U.S. Cl. .................................. 585/315; 585/329; 585/330; 585/331; 585/332
[58] Field of Search ............... 585/315, 329, 330, 331, 585/332

[56] References Cited

U.S. PATENT DOCUMENTS

| | | | |
|---|---|---|---|
| 2,999,074 | 9/1961 | Bloch et al. | 252/442 |
| 3,050,472 | 8/1962 | Morrell | 252/435 |
| 3,050,473 | 8/1962 | Morrell | 252/435 |
| 3,112,351 | 11/1963 | Hoekstra | 585/748 |
| 3,128,319 | 4/1964 | Meisinger et al. | 585/734 |
| 3,132,109 | 5/1964 | Morrell | 252/435 |
| 3,283,021 | 11/1966 | Hardison | 585/394 |
| 3,402,130 | 9/1968 | Nixon | 252/437 |
| 3,437,706 | 4/1969 | Gantt et al. | 585/450 |
| 3,437,707 | 4/1969 | Sulzbach | 585/450 |
| 3,437,708 | 4/1969 | Gantt | 585/450 |
| 3,506,733 | 4/1970 | Mayhue | 585/737 |
| 3,510,534 | 5/1970 | Sulzbach | 585/450 |
| 3,527,715 | 9/1970 | Giannetti et al. | 252/415 |
| 3,649,704 | 3/1972 | Hayes | 585/482 |
| 3,652,697 | 3/1972 | Hayes | 585/482 |
| 3,789,082 | 1/1974 | Cook et al. | 585/748 |
| 3,916,019 | 10/1975 | Closson et al. | 585/511 |
| 3,959,400 | 5/1976 | Lucki | 585/515 |
| 4,098,839 | 7/1978 | Wilms et al. | 585/526 |
| 4,113,790 | 9/1978 | Cesca et al. | 585/532 |

Primary Examiner—Curtis R. Davis
Attorney, Agent, or Firm—James R. Hoatson, Jr.; John F. Spears, Jr.; William H. Page, II

[57] ABSTRACT

An improved butane isomerization process which decreases the rate of catalyst deactivation is disclosed. A normal butane feed stream which contains small amounts of isobutylene is passed through a polymerization zone wherein the isobutylenes are converted into heavier hydrocarbons. The polymerization zone effluent is passed into the deisobutanizer column in which the isomerization zone effluent is separated for the recovery of the product isobutane. Heavy hydrocarbons are removed as a net bottoms stream and the remaining fresh feed components become part of the normal butane recycle stream removed from the deisobutanizer as a sidecut stream.

6 Claims, 1 Drawing Figure

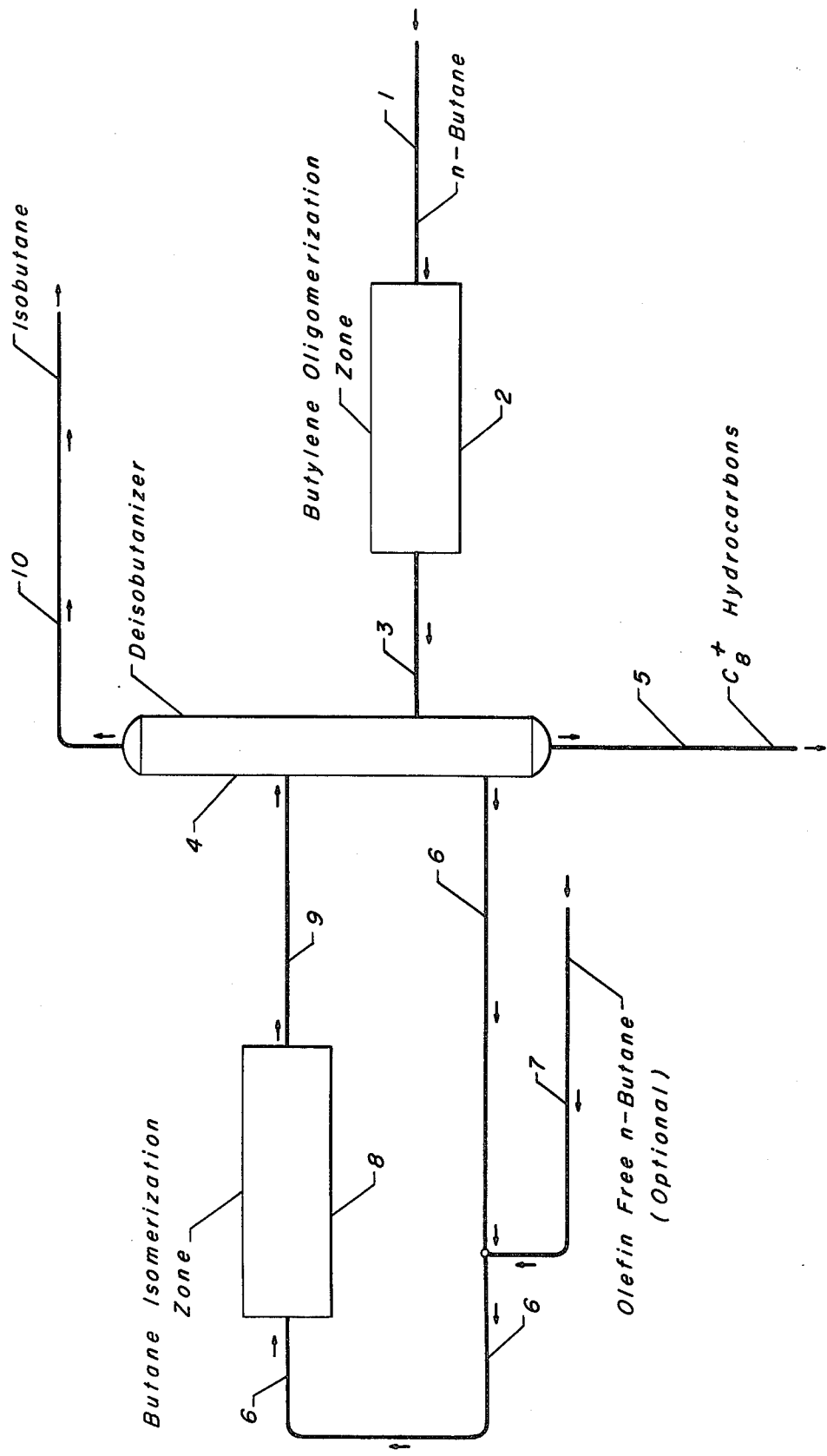

BUTANE ISOMERIZATION PROCESS

FIELD OF THE INVENTION

The invention relates to the broad area of hydrocarbon conversion processing such as performed in petroleum refineries and petrochemical plants. The invention more specifically relates to normal paraffin isomerization and olefinic hydrocarbon dimerization processes. Such dimerization processes are also referred to as catalytic condensation or polymerization processes. The invention is specifically directed to an improved process for the isomerization of normal butane into isobutane.

PRIOR ART

Both the isomerization of normal paraffins and the dimerization or polymerization of light olefins are well known processes which are in widespread commercial use.

In many butane isomerization processes a liquid-phase isomerization zone effluent stream is formed by condensing most of the butanes in the isomerization reactor and separating the thus formed liquid from uncondensed hydrogen and any light gases. The liquid-phase isomerization zone effluent stream is then passed into a deisobutanizer column, with isobutanes being removed as an overhead stream and a normal butane recycle stream being removed as a bottoms stream. This butane recycle stream is then combined with the butane fresh feed stream and recycle hydrogen and passed into the isomerization reactor.

It is an accepted practice to pass a butane fresh feed stream which comprises an appreciable amount of isobutane into the deisobutanizer of a butane isomerization zone. This allows the direct recovery of this isobutane and improves the conversion rate within the isomerization zone as compared to passing the feed stream directly into the isomerization zone.

Processes for the dimerization (oligomerization) of light olefins using a heterogeneous catalyst are described in U.S. Pat. Nos. 3,916,019 (Cl. 260-683.15E); 3,959,400 (Cl. 260-683.15R); 4,098,839 (Cl. 260-683.15D) and 4,113,790 (Cl. 260-683.15B). Process flow diagrams for oligomerization processes which utilize a solid phosphoric acid (SPA) catalyst are presented in U.S. Pat. Nos. 3,437,706; 3,437,707; 3,437,708; and 3,510,534 (all former Cl. 260-671).

Solid phosphoric acid catalysts are described in U.S. Pat. Nos. 3,050,472; 3,050,473; 3,132,109 (all Cl. 252-435) and 3,402,130 (Cl. 252-437).

The isomerization of normal paraffins is described in U.S. Pat. Nos. 2,999,074; 3,112,351; 3,128,319; 3,283,021 (Cl. 260-666); 3,527,715 (Cl. 252-415); 3,649,704 (Cl. 260-668A); 3,652,697 (Cl. 260-668A); 3,789,082 (Cl. 260-683.68); and 3,506,733 (Cl. 260-683.68).

BRIEF SUMMARY OF THE INVENTION

The invention provides an improved butane isomerization process in which catalyst deactivation caused by isobutylene in the butane feed stream is greatly reduced or eliminated completely. In the subject process the isobutylene, and any other light olefin present in the feed stream is reacted to form much heavier hydrocarbons, such as $C_8$-plus hydrocarbons, in an upstream oligomerization zone. The resultant oligomerization zone effluent stream is passed into a deisobutanizer in which the heavy hydrocarbons are separated out as a bottoms stream. This leaves butylene free normal butanes which are charged to the isomerization zone as part of a recycle stream as a sidecut stream.

One embodiment of the invention may be characterized as a hydrocarbon conversion process which comprises the steps of passing a feed stream which is rich in normal butane and comprises between 0 and about 1.5 mole percent butylenes into an oligomerization zone and thereby producing an oligomerization zone effluent stream which is rich in normal butanes and comprises a small amount of $C_8$ and $C_{12}$ hydrocarbons resulting from the reaction of said butylenes; passing the oligomerization zone effluent stream into a fractionation zone; removing a recycle stream which is rich in normal butane from the fractionation zone and passing the recycle stream into a butane isomerization zone to produce an isomerization zone effluent stream comprising isobutane and normal butane; passing the isomerization zone effluent stream into the fractionation zone; removing a net overhead stream which is rich in isobutane from the fractionation zone; and removing a net bottoms stream comprising $C_8$ hydrocarbons from the fractionation zone.

BRIEF DESCRIPTION OF THE DRAWING

The Drawing illustrates the preferred embodiment of the invention. A concentrated normal butane feed stream which contains a small amount of butylenes including isobutylene as impurities enters the process through line 1 and is passed into a butylene oligomerization zone 2. In this zone, the entering hydrocarbons are contacted with a bed of oligomerization-promoting catalyst maintained at the proper conditions to effect the oligomerization of substantially all of the butylene and other light olefins present in the feed stream. This produces an oligomerization zone effluent stream carried by line 3 which contains the normal butane originally present in the feed stream of line 1 and a small amount of $C_8$ and heavier hydrocarbons. The oligomerization zone effluent stream is passed into a deisobutanizer column 4 at a lower intermediate point.

The heavy hydrocarbons which enter the deisobutanizer are concentrated into a net bottoms stream which is removed from the deisobutanizer in line 5. The more volatile normal butane is concentrated into a sidecut stream which is removed from the deisobutanizer in line 6 and passed into a butane isomerization zone 8. Any olefin-free normal butane which it is desired to charge to the isomerization zone may be passed into the process through optional line 7. In the isomerization zone the entering stream of normal butanes is contacted with a bed of isomerization-promoting catalyst maintained at isomerization conditions to produce a net effluent stream which is a mixture of normal and iso butanes.

This isomerization zone effluent stream is passed into the deisobutanizer at an upper intermediate point through line 9. The more volatile isobutane travels upward through the column and is concentrated into a net overhead stream which is rich in isobutane and is removed from the column in line 10. The normal butane present in the butane isomerization zone effluent stream travels downward through the deisobutanizer column and is withdrawn through line 6 for another passage through the isomerization zone. This description of the preferred embodiment of the invention is not intended to preclude from the scope of the subject invention those other embodiments which are set out herein or which are the result of normal and expected modification to those embodiments.

DETAILED DESCRIPTION

The increasing demand for high octane unleaded gasoline has resulted in increased utilization of butane isomerization processes. These processes are used to convert the large amounts of natural and by-product normal butane into isobutane, which may then be alkylated with a light olefin to produce C7-plus branched chain hydrocarbons having a good octane rating. Isobutane may also be charged to a dehydrogenation zone to produce isobutylene, which could be oxidized or charged to a process for the production of methyl tertiary butyl ether to produce other high octane blending components. A second factor which is leading to increased demand for butane isomerization capacity is a large amount of natural butane which is now being recovered from petroleum deposits but was previously flared at the wellhead or crude processing site. The transportation of these butanes is both easier and cheaper if they are consumed in a reaction, such as alkylation, which produces a normally liquid hydrocarbon.

The feed stream to a butane isomerization process is normally a stream which is rich in normal butanes but which also contains some other hydrocarbons including $C_5$ hydrocarbons and butylenes including isobutylene. This stream is often referred to as a field butane stream. The separation of the $C_5$ hydrocarbons from the $C_4$ hydrocarbons is achieved quite readily in a fractionation column, with this column normally being the deisobutanizer of the isomerization zone. However, the relative volatility of isobutylene is between those of isobutane and normal butane. Therefore, if the deisobutanizer is operated to produce a very high purity isobutane overhead stream any isobutylene which enters as part of the feed stream will be withdrawn from the column as part of the next lower stream, which is normally the normal butane recycle stream. The isobutylene is thereby concentrated into a stream which is charged to the isomerization reactor. This has been found to be undesirable as it accelerates the deactivation of the preferred butane isomerization catalyst.

It is an objective of this invention to provide an improved butane isomerization process. It is a further objective of this process to provide a butane isomerization process which is not adversely affected by the presence of isobutylene in the feed stream. It is also an objective of the invention to provide a low cost and simple method to remove isobutylene from the field butanes charged to a normal butane isomerization zone.

The feed stream to the subject process may contain a mixture of isobutane and normal butanes as found in most natural gas or it may contain only normal butane. The feed stream will normally be a mixture of hydrocarbons including $C_5$ hydrocarbons. It is preferred that the feed stream contains as little $C_5$-plus hydrocarbons as practical and contains over 95 mole percent $C_4$ hydrocarbons. From 0.0 to about 5.0 mole percent isobutylene may be present in the feed, which is preferably rich in normal butane. As used herein the term "rich" is intended to indicate that the concentration of the specified substance in the subject stream is greater than 60 mole percent. Preferably, the feed stream will contain between 0.0 and 1.5 mole percent isobutylene. The butylene content of the feed butane stream will vary with its source, with higher butylene levels being found in streams derived from fluidized catalytic cracking units or thermal cracking units.

In the practice of the subject invention the feed stream is passed directly into an oligomerization zone. Similar zones are also referred to as dimerization or catalytic condensation zones. The dimerization zone may take many forms depending on such variables as the type of catalyst employed within the zone. Heterogeneous catalytic systems for the production of higher molecular weight olefins by the oligomerization or dimerization of light olefins are described in U.S. Pat. Nos. 3,906,053; 3,916,019; 3,959,400; 3,981,940 and 3,981,941. As may be expected from the large number of available processes, the conditions employed within the reaction zone may vary widely. For instance, the just cited references specify that the reaction may be performed at temperatures ranging from $-50°$ C. to $250°$ C. and at a pressure ranging from about 1.3 atmospheres gauge to approximately 100 atmospheres gauge.

The preferred catalyst for use in the oligomerization zone is an SPA (solid phosphoric acid) type catalyst. As used herein, the term "SPA catalyst" is intended to indicate a solid catalyst which contains as one of its principal ingredients an acid of phosphorus such as an ortho-, pyro- or tetra-phosphoric acid. The catalyst is normally formed by mixing the acid of phosphorus with a siliceous, solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives, such as mineral talc, fullers earth and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this such as a lower phosphoric acid content are possible. Further details as to the composition and production of SPA catalysts may be obtained from U.S. Pat. Nos. 3,050,472; 3,050,473 and 3,132,109 and from other references.

The catalyst is preferably disposed in fixed beds within the reactor of the oligomerization zone. Either a tubular or chamber-type reactor structure may be used. In a tubular reactor, the catalyst is placed in relatively small diameter tubes which are surrounded by a water jacket to remove the heat liberated by the exothermic reaction. Any steam generated in this manner can be used to preheat the feed. In a chamber-type reactor, the reactants flow through a series of large diameter catalyst beds. In commercial units in which the feed stream has a high olefin concentration, the temperature of the reactants is controlled by recycling relatively inert hydrocarbons which act as a heat sink or by the use of a quench between vertically stacked catalyst beds. The quench material is the same as that used as the recycle stream, and both methods of temperature control may be used simultaneously. The relatively very low olefin concentration in the feed stream of the subject process eliminates the need for quenching the reaction zone, and the normal butane present in the feed stream makes recycling inert hydrocarbons unnecessary. The different catalyst beds are preferably contained within a single, cylindrical, vertically oriented vessel, and the feed stream preferably enters the top of the reactor. A chamber-type reactor containing five or less catalyst beds is preferred.

The oligomerization zone is maintained at conditions which may vary widely due to the previously listed variables. A broad range of suitable conditions includes a L.H.S.V. of about 0.5 to 4 hr, and a pressure from about 15 psig. to about 1200 psig., with a preferred pressure range for an SPA catalyst being from 100 to 1000 psig. The temperature maintained in this zone with the preferred SPA catalyst may vary from about 140° C. to about 260° C. The especially preferred oligomerization conditions are a liquid hourly space velocity of 1.0, a temperature of about 170° C. and a pressure of about 450 psig. Steam or water may be fed into the reactor to maintain the desired water content in the preferred catalyst. It is preferred that the oligomerization zone contains no fractionation columns, vapor-liquid separators or other means to separate or purify the effluent stream.

Passing the feed stream through the oligomerization zone at these conditions will result in substantially all of the butylenes present in the feed stream being converted into heavier hydrocarbons. These hydrocarbons will be predominantly $C_8$ and $C_{12}$ straight and branched chain hydrocarbons which may be used as motor fuel. The maximum total concentration of $C_8$ and $C_{12}$ hydrocarbons in the oligomerization zone effluent stream is expected to be less than 2.5 mole percent and is preferably less than 1.0 mole percent. Substantially all of the remainder is normal butane. The effluent of the oligomerization reactor is therefore substantially free of isobutylene and may be passed directly into the fractionation zone. Preferably, this zone comprises a single fractionation column although two columns could be employed. The fractionation zone is commonly referred to as the deisobutanizer since its principal function is to concentrate any entering isobutane into a net overhead stream which is removed from the process as the product stream. When properly designed and operated a column containing about 75 sieve trays will function adequately as the deisobutanizer column. Substantially all of the $C_5$-plus hydrocarbons present in the feed stream and those formed in the oligomerization zone are removed from the deisobutanizer as a net bottoms stream. The remaining normal butane, together with a very small amount of $C_5$-plus hydrocarbons, is removed from the deisobutanizer as sidecut stream at a lower intermediate point below the intermediate point at which the oligomerization zone effluent stream enters the column. This recycle stream becomes the feed stream to the isomerization zone. If a high purity normal butane stream which does not contain an unacceptable amount of butylenes is present this stream may be admixed with the recycle stream or passed into the isomerization zone separately.

The normal butane rich stream removed from the deisobutanizer is passed into a butane isomerization zone. This zone comprises a reactor and auxiliary process equipment such as heaters, condensers, separatory vessels, etc. The isomerization zone normally contains a stripping column which eliminates hydrogen and light ends (methane and ethane) from the effluent of the isomerization reactor. With the preferred catalyst, this stripping column will also eliminate volatile chloride compounds from the isomerization zone effluent. The entering butane is passed through a drying zone, which preferably uses molecular sieves as the drying agent, heat exchanged against the reactor effluent and then further heated to the desired temperature prior to being passed into the reactor.

The core of the operation of the isomerization zone is the passage of the sidecut stream through a reactor maintained at butane isomerization-promoting conditions including the presence of an acidic isomerization catalyst. This is normally a relatively low pressure operation performed at a pressure of from about 50 to 600 psig. and at an elevated temperature as required by the activity of the catalyst. The average reactant temperature may be as high as 400° C., but is preferably between 100° C. and 320° C. It is normal practice to pass the butane through the reactor in admixture with between 0.5 and 10 moles of hydrogen per mole of butanes to ensure vapor phase conditions and to suppress coke deposition on the catalyst. It is preferred that the butane is passed vertically through one or more fixed beds of catalyst located within the reactor at a liquid hourly space velocity between 1.0 and 6.0, but space velocities in the broad range of 0.5 to 12.0 can be employed if desired.

The effluent of the isomerization reactor is normally partially condensed and then separated into a hydrogen-rich recycle gas which is returned to the reactor and an isomerate-containing liquid stream. This liquid is passed into the stripping column, with the stripping column bottoms becoming the isomerization zone effluent stream. The net hydrocarbon effluent of the isomerization zone is a mixture of isobutane and normal butane. Substantially all of the isobutane which enters the deisobutanizer is concentrated into a net overhead stream. The unconverted normal butane becomes part of the sidecut stream and is recycled to extinction through the isomerization zone. Further details on the butane isomerization step of the subject process may be obtained by referring to the previously cited references.

The preferred isomerization-promoting catalyst for use in the isomerization zone comprises a platinum group component and a halogen component supported by an inorganic oxide carrier. In general, the carrier material is a porous, high surface area material which is relatively refractory to the conditions utilized in the isomerization process. The carrier material may be selected from silica, alumina, titanium dioxide, chromium, or mixtures of these oxides; various naturally occurring refractory oxides in different degrees of purity, such as bauxite and bentonite clay; or a diatomaceous earth such as kieselguhr. Of the above-mentioned oxides, alumina is preferred and particularly preferred is a synthetically prepared substantially anhydrous gamma-alumina with a high degree of purity.

The preferred platinum group component is platinum, palladium or a mixture of platinum and palladium. This however is not intended to exclude the other platinum group metals such as rhodium, ruthenium, osmium and iridium. A platinum group component may exist within the final catalytic composite as an oxide, a sulfide or a halide, etc., or as an elemental metal. On a weight basis, the platinum group component will comprise only a minor fraction of the total catalytic material. The preferred catalyst will therefore contain less than about 2.0 wt.% of the platinum group component, with the preferred concentration being from about 0.05 to about 1.0 wt.%. The method by which the platinum group component is made part of the catalytic composite is not controlling. It may therefore be added by co-precipitation or cogellation with the preferred carrier material or by ion-exchange or impregnation on pre-existing carrier material. The preferred method of preparing the catalyst impregnates the carrier material by contacting it with an aqueous solution of a water-soluble, decomposable compound of a platinum group metal. This may be performed by dipping the carrier material in a solution of chloroplatinic acid, ammonium chloroplatinate, bromoplatinic acid, or platinum dichloride. The utilization of a platinum chloride compound is preferred since it facilitates the incorporation of both the platinum component and at least a minor quantity of the halogen component in a single step.

There are also numerous ways in which to add the halogen component to the isomerization catalyst. The halogen component may be composited with the carrier material during the impregnation of the carrier material with the platinum group component by the utilization of a mixture of chloroplatinic acid and hydrogen chloride. Alternatively, the alumina hydrosol which is typically utilized to form the preferred alumina carrier material may contain at least a portion of the halogen. The halogen may also be added by contacting a calcined carrier material with an aqueous solution of an acid such as hydrogen chloride, hydrogen, fluoride, or hydrogen bromide, etc. The halogen component may be selected from chlorine, fluorine, iodine, bromine or mixtures thereof with chlorine and fluorine being particularly preferred. The halogen component is normally referred to as a combined halogen and is typically present in an amount of from 0.01 to about 5.0 wt.% based on the dried support material.

A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically adsorbed solvents such as water but to retain some chemically combined hydroxyl groups on the surface of the catalyst. Temperatures ranging from 350° C. to about 700° C. are usually satisfactory. The calcined composite is then reacted with a metal halide of the Friedel-Crafts type. Suitable metal halides include aluminum chloride, aluminum bromide, ferric chloride and zinc chloride, etc. Of these, aluminum chloride is particularly preferred.

Recently developed isomerization catalysts are of a bimetallic or trimetallic nature. An example of this is the catalytic composite comprising a platinum group component, a germanium component, and a Friedel-Crafts metal halide component shown in U.S. Pat. No. 3,649,704. In U.S. Pat. No. 3,652,697, there is disclosed a trimetallic catalyst comprising a platinum group component, a germanium component, a rhenium component and a Friedel-Crafts metal halide component.

I claim as my invention:

1. In a process for the isomerization of normal butanes wherein a recycle stream which is rich in normal butane is withdrawn from a deisobutanizer column and is then passed into a butane isomerization zone, a butane isomerization zone effluent stream which comprises isobutane and normal butane is passed into the deisobutanizer column, and a product stream which is rich in isobutane is withdrawn from the deisobutanizer column; the improvement which comprises passing a fresh feed stream to the butane isomerization zone, which comprises isobutylene and is rich in normal butane, through an oligomerization zone and thereby producing an oligomerization zone effluent stream which is rich in normal butane and comprises $C_8$ hydrocarbons, passing the oligomerization zone effluent stream into the deisobutanizer column, and removing a net bottoms stream comprising $C_8$ hydrocarbons from the deisobutanizer column.

2. A butane isomerization process which comprises the steps of:
   (a) passing a butane feed stream which is rich in normal butane and comprises between 0 and 5.0 mole percent butylenes into an oligomerization zone maintained at oligomerization conditions and producing an oligomerization zone effluent stream which is rich in normal butanes and comprises $C_8$ hydrocarbons;
   (b) passing the oligomerization zone effluent stream into a fractionation zone;
   (c) removing a recycle stream which is rich in normal butane from the fractionation zone;
   (d) passing the recycle stream into a butane isomerization zone maintained at butane isomerization conditions and producing an isomerization zone effluent stream comprising isobutane and normal butane;
   (e) passing the isomerization zone effluent stream into the fractionation zone;
   (f) removing a net overhead stream which is rich in isobutane from the fractionation zone; and
   (g) removing a net bottoms stream comprising $C_8$ hydrocarbons from the fractionation zone.

3. The process of claim 2 further characterized in that a second butane feed stream which is substantially free of butylenes is passed directly into the butane isomerization zone.

4. The process of claim 2 further characterized in that the butane feed stream comprises between 0 and 1.5 mole percent isobutylene.

5. The process of claim 4 further characterized in that the fractionation zone comprises a single fractionation column.

6. The process of claim 5 further characterized in that the net bottoms stream is rich in $C_8$ hydrocarbons.

* * * * *